United States Patent
Nason et al.

(10) Patent No.: US 7,226,278 B2
(45) Date of Patent: Jun. 5, 2007

(54) SHAPE MEMORY ALLOY WIRE DRIVEN POSITIVE DISPLACEMENT MICROPUMP WITH PULSATILE OUTPUT

(75) Inventors: Clyde K. Nason, Valencia, CA (US); William H. Stutz, Jr., Eagle Rock, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 0 days.

(21) Appl. No.: 11/230,142

(22) Filed: Sep. 19, 2005

(65) Prior Publication Data

US 2006/0013716 A1    Jan. 19, 2006

Related U.S. Application Data

(63) Continuation of application No. 10/127,094, filed on Apr. 22, 2002.

(51) Int. Cl.
*F04B 17/00* (2006.01)
*F04B 35/00* (2006.01)
*F04B 49/06* (2006.01)

(52) U.S. Cl. ............... 417/410.1; 417/321; 417/53
(58) Field of Classification Search ............... 417/321, 417/53, 410.1; 74/111, 126
See application file for complete search history.

(56) References Cited

U.S. PATENT DOCUMENTS

| | | | |
|---|---|---|---|
| 3,488,763 A | | 1/1970 | Lofquist |
| 4,332,246 A | * | 6/1982 | Thomson ............... 604/28 |
| 4,573,994 A | | 3/1986 | Fischell et al. |
| 4,646,523 A | | 3/1987 | O'Hare |
| 4,761,955 A | * | 8/1988 | Bloch ............... 60/528 |
| 4,811,564 A | | 3/1989 | Palmer |
| 4,886,499 A | | 12/1989 | Cirelli et al. |
| 4,930,993 A | * | 6/1990 | Han et al. ............... 417/226 |

(Continued)

FOREIGN PATENT DOCUMENTS

EP    0 462 508 A1    12/1991

(Continued)

OTHER PUBLICATIONS

Schnabel, N.M., Shape Memory Alloy Inchworm Actuator, Jun. 14, 1989, Mechanical Engineering Department California Polytechnic State University, San Luis Obispo, CA 39 pages.

*Primary Examiner*—Micahel Koczo
*Assistant Examiner*—Ryan Gillan
(74) *Attorney, Agent, or Firm*—Gates & Cooper LLP

(57) ABSTRACT

Apparatuses and methods for pumping fluid are disclosed. An exemplary apparatus is a miniature pump that includes a shape memory wire that obtains a plastic condition below a transformation temperature and has a memorized shape such that the shape memory wire produces a work stroke by returning to the memorize shape at least at the transformation temperature. A spring biased against the shape memory wire is deflected by the work stroke to deform the shape memory wire from the memorized shape below the transformation temperature. A fluid pump is coupled to the shape memory wire and driven by the biased spring and shape memory wire to produce a fluid flow. The miniature pump can be incorporated into a self-contained infusion device in the form of a compact self-adhesive patch including a fluid reservoir, control electronics and power supply that is place directly at the infusion site of a user.

24 Claims, 18 Drawing Sheets

U.S. PATENT DOCUMENTS

| | | | |
|---|---|---|---|
| 4,955,196 A | 9/1990 | Lin et al. | |
| 5,049,141 A | 9/1991 | Olive et al. | |
| 5,178,609 A | 1/1993 | Ishikawa | |
| 5,207,645 A | 5/1993 | Ross et al. | |
| 5,238,022 A * | 8/1993 | Zink | 137/554 |
| 5,622,482 A | 4/1997 | Lee | |
| 5,626,581 A | 5/1997 | Stachlin et al. | |
| 5,704,520 A | 1/1998 | Gross | |
| 5,816,306 A * | 10/1998 | Giacomel | 160/6 |
| 5,820,589 A | 10/1998 | Torgerson et al. | |
| 5,919,167 A | 7/1999 | Mulhauser et al. | |
| 5,961,496 A | 10/1999 | Nielson et al. | |
| 6,033,412 A | 3/2000 | Losken et al. | |
| 6,157,101 A | 12/2000 | Ullakko | |
| 6,200,317 B1 | 3/2001 | Aalsma et al. | |
| 6,375,638 B2 | 4/2002 | Nason et al. | |
| 6,485,461 B1 | 11/2002 | Mason et al. | |
| 6,530,217 B1 | 3/2003 | Yokota et al. | |

FOREIGN PATENT DOCUMENTS

| | | |
|---|---|---|
| EP | 0 709 573 A1 | 5/1996 |
| JP | 0 435 3272 | 12/1992 |

* cited by examiner

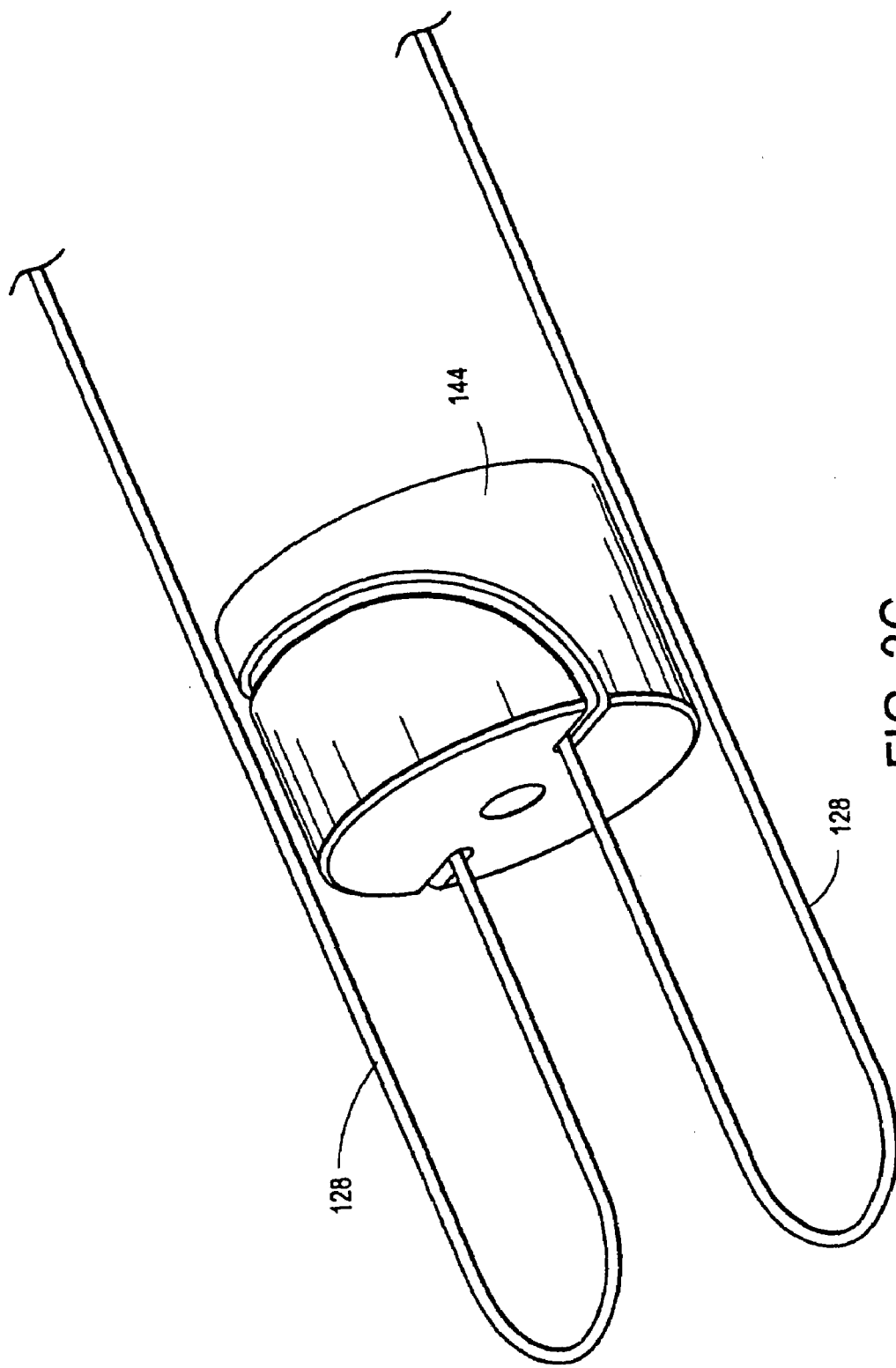

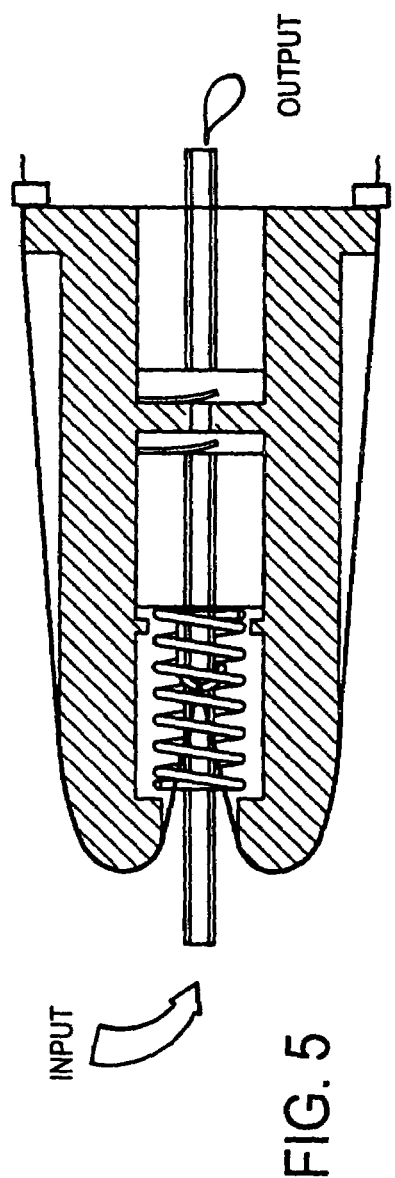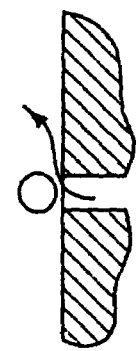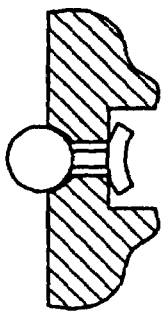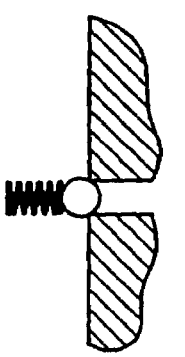

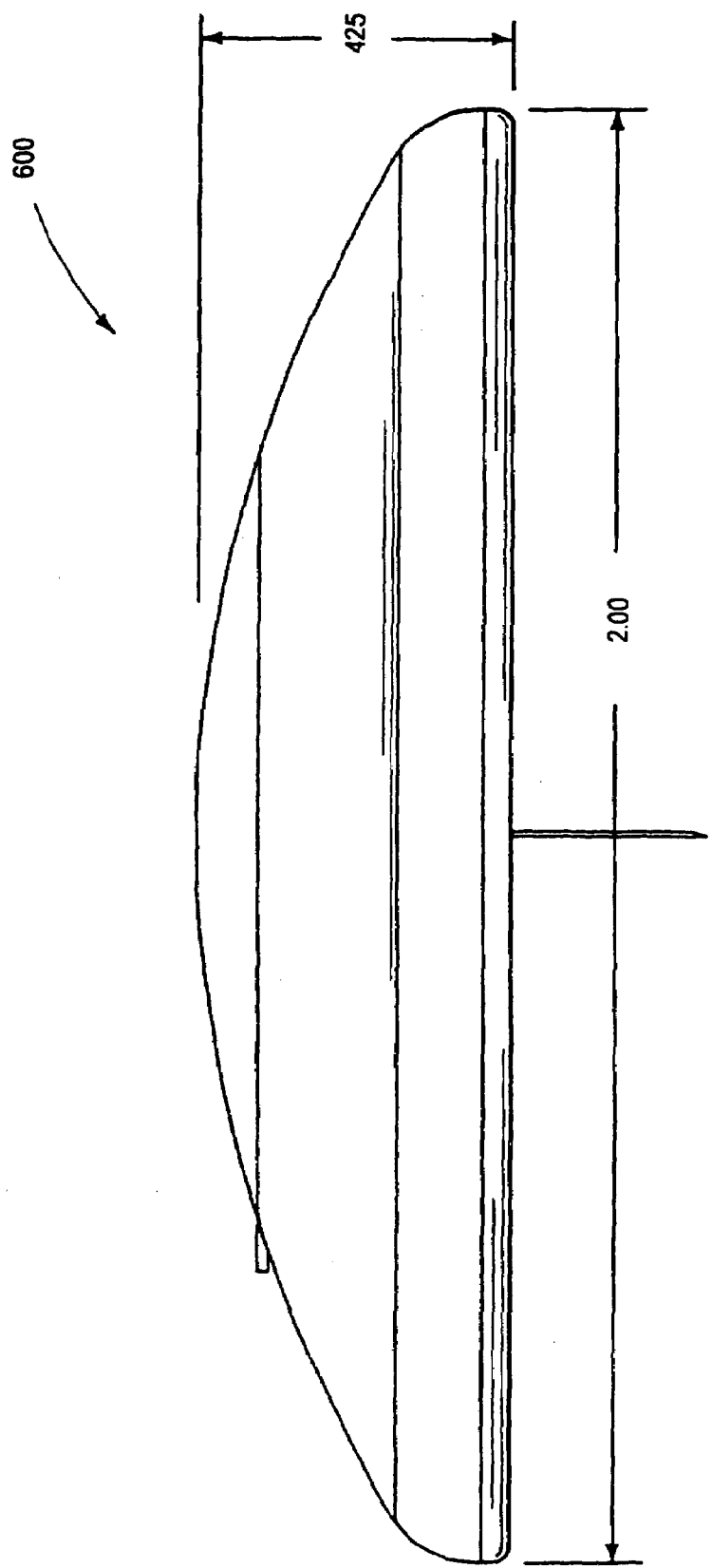

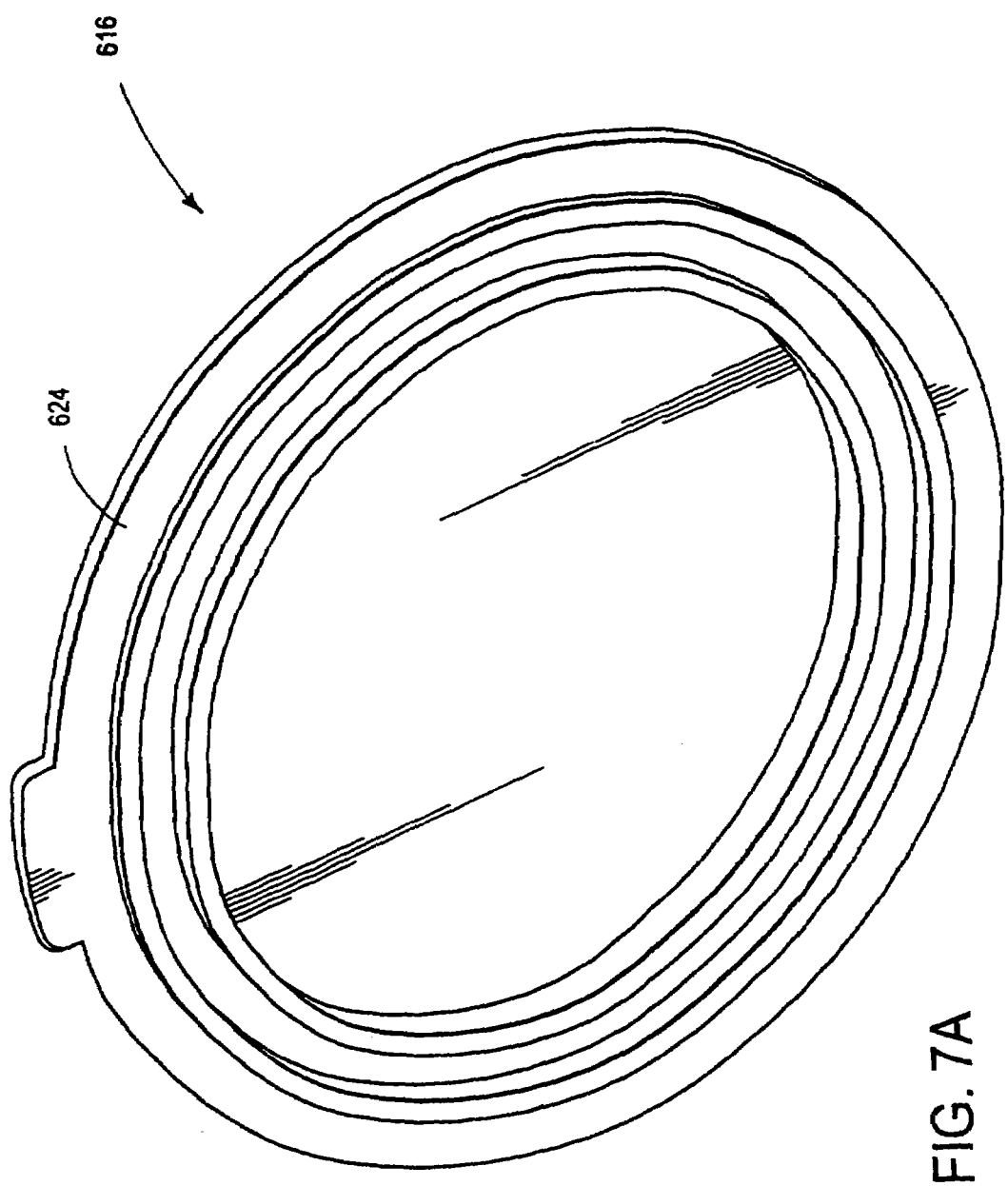

SHAPE MEMORY ALLOY WIRE DRIVEN POSITIVE DISPLACEMENT MICROPUMP WITH PULSATILE OUTPUT

CROSS-REFERENCE TO RELATED APPLICATIONS

This application is a continuation application of U.S. patent application Ser. No. 10/127,094, filed Apr. 22, 2002, the entire contents of which are incorporated herein by reference. This application cross-references U.S. patent application Ser. No. 09/249,666, filed Feb. 12, 1999, (now U.S. Pat. No. 6,375,638) by Clyde K. Nason and William H. Stutz, Jr. and entitled "INCREMENTAL MOTION PUMP MECHANISMS POWERED BY SHAPE MEMORY ALLOY WIRE OR THE LIKE", the entire contents of which are incorporated herein by reference.

BACKGROUND OF THE INVENTION

1. Field of the Invention

This invention relates generally to devices and methods for conveying small amounts of fluids. More specifically, this invention relates to compact medical devices used to convey medications, such as the insulin infusion pumps used in the treatment of diabetes.

2. Description of the Related Art

Fluid pumps in various forms are employed in a wide range of applications. In the medical arts, precise mechanisms are often required to deliver small fluid amounts accurately and reliably.

A variety of mechanisms that are used to convey fluids have been developed for infusion devices. Typically these devices employ electrical motors. Over time, portable infusion devices have evolved into small self-contained medication deliver systems, which, due to the size demands of the internal components, are generally about the size of an electronic pager. A large part of such infusion devices consists of the battery and fluid drive mechanism. As there is a desire for even smaller, more inconspicuous and less cumbersome infusion devices, there is a need smaller fluid driving systems which can utilize smaller batteries.

In addition, because traditional infusion devices typically include expensive and sensitive components, it is not cost effective to use such mechanisms in a disposable device. In view of the foregoing, there is a need in the art for smaller, robust fluid driving systems. There is also a need for ultra compact infusion devices. In addition, there is a need for devices and systems that are inexpensive, reusable and disposable. Embodiments of the invention disclosed herein meet these needs.

SUMMARY OF THE INVENTION

The invention disclosed herein has a number of embodiments. Typical embodiments of the invention include a miniature positive displacement fluid "pump" that is driven by a shape memory alloy wire to produce a pulsatile output. Embodiments of the invention allow for an accurate, repeatable and reliable fluid output using a minimum number of components. The miniature positive displacement type of pump mechanisms disclosed herein are suitable for the precise delivery of a variety of liquid medication such as insulins. Moreover, embodiments of the invention can be constructed almost entirely from plastic components at an extremely low cost. As embodiments of the invention require very little power to operate they are especially useful for long term pump applications.

One embodiment of the invention is a positive displacement-type miniature pump where the reciprocal motion used to drive the pump is provided by a shape memory alloy (SMA) wire. In such embodiments, the SMA wire is typically activated by a low voltage source, such as a battery, that is applied to the wire to cause it to thermoelectrically heat until reaching a transformation temperature. Upon reaching the transformation temperature, work is performed by the wire as it undergoes a transformation from a plastic condition to return to a preset "memorized" shape. Removal of the voltage source allows the wire to return to the plastic condition so that a force exerted by a bias spring can deform the wire in preparation for a repeated work stroke. Application of the voltage source is pulsed by an electronic timing circuit to produce continuous pulsed work stroke and, in this manner, drive a fluid flow.

Preferred embodiments of the invention employ a miniature pump (such as the one previously described) in a compact infusion device. Such embodiments include a multi-day (e.g., three-day) disposable device that employs a collapsible drug fluid reservoir bag, a reusable electronics module to control fluid delivery and a piercing member (such as a needle) to directly deliver medication subcutaneously to a user. Typically the assembly in such embodiments is housed in a convex plastic "turtle shell" enclosure. In preferred embodiments, the reservoir is fitted with a septum to allow the user to conveniently refill the device. In operation, the infusion device can be placed directly on the skin (e.g. at the infusion site of the user) and held there by a pressure sensitive adhesive material on the back of the base plate.

BRIEF DESCRIPTION OF THE DRAWINGS

Referring now to the drawings in which like reference numbers represent corresponding parts throughout:

FIG. 3C illustrates details of the SMA wire connection to the piston of one embodiment of the invention;

FIGS. 5A–5F illustrate various embodiment of suitable valves for the pump chamber;

FIG. 6D illustrates a exterior side view of the compact infusion device;

FIG. 7A illustrates a view of the electronics module of the compact infusion device;

DETAILED DESCRIPTION OF THE PREFERRED EMBODIMENT

1. Overview

Figure 1A:
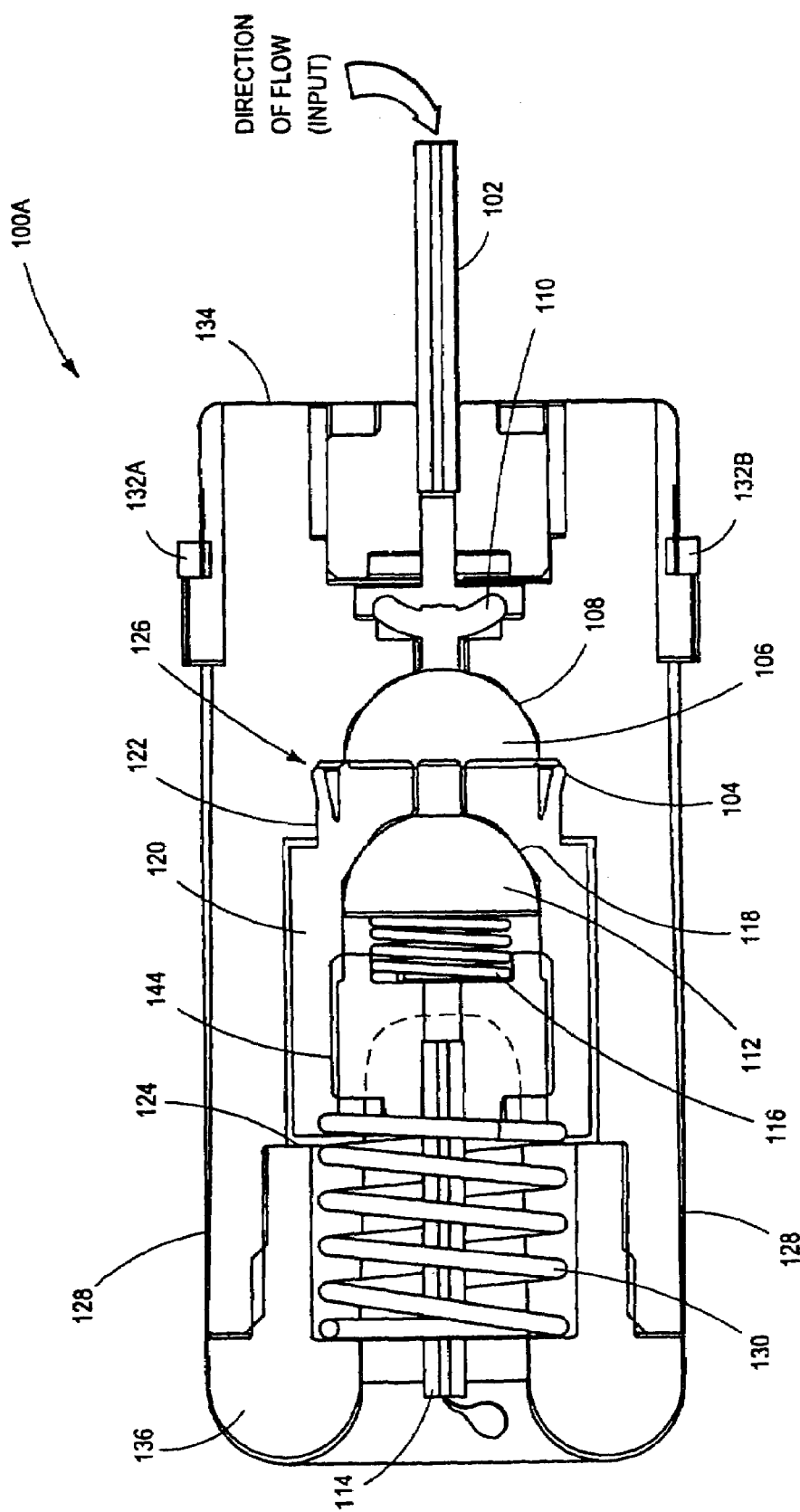
FIG. 1A is a longitudinal cross-section of an exemplary embodiment of the invention showing the internal components.

The invention disclosed herein has a number of embodiments. An illustrative embodiment of the invention disclosed herein is a positive displacement-type miniature pump that employs a mechanism which includes a shape memory alloy (SMA) material. Shape memory alloys are metals known for unusual and dramatic property changes with temperature. Selective alloying of the metal determines a transformation temperature at which the alloy transitions as it is heated from a martensite crystal structure to an austentite crystal structure. Below the transformation temperature, in the martensitic phase, the alloy is easily deformed in a plastic condition. However, when the alloy is heated to a temperature at or exceeding the transformation temperature, internal stresses drive the alloy to return to the memorized shape in the austentitic phase. During the shape recovery, work energy can also be harnessed at very high stress levels. The "memory" of the alloy is set with a very high temperature treatment (well above the transformation temperature) to fix the crystallographic structure of the alloy.

A common shape memory material is a nickel-titanium alloy comprising nearly equal amounts of each element. As is known in the art, other alloying elements can also be used to obtain particular properties as well. In addition, other materials such as CuAlNi are also known to exhibit the shape memory effect. Nickel-titanium is particularly desirable because it also possesses very good electrical characteristics. In a wire form, an electric current can be applied to the material to provide direct thermoelectric heating. As a result, separate heaters are not required to activate the material.

A preferred embodiment of the invention is a positive displacement-type miniature pump that employs a nickel-titanium shape memory alloy material. The reciprocal motion needed to drive the pump is provided by a shape memory alloy wire, manufactured from an SMA material such as NITINOL (an acronym for "nickel titanium naval ordinance laboratory", for its material composition and discovery locale). In such embodiments, the SMA wire is activated by a low voltage source, such as a direct current (DC) battery, applied to the wire to cause the wire to thermoelectrically heat until reaching a transformation temperature. Upon reaching the transformation temperature, work is performed by the wire as it undergoes a transformation from a plastic condition to return to a preset "memorized" shape. Modulation of the voltage source allows the wire to cool below the transformation temperature and return to the plastic condition so that a force exerted by a bias spring can deform the wire in preparation for a repeated work stroke. Typically, embodiments of the invention will use a shape memory alloy material having a transformation temperature above ambient conditions, and preferably well above body temperature to accelerate cooling of the wire (and thereby accelerate pumping). However, too high a transformation temperature may require higher power consumption by the pump. Application of the voltage source is pulsed by an electronic timing circuit to produce continuous pulsed work stroke and drive a fluid from the pump.

2. Shape Memory Alloy Wire Driven Positive Displacement Micro Pump

Embodiments of the invention include a miniature positive displacement type pump mechanism suitable for the precise delivery of liquid medication such as insulin. The pump can achieve an accurate and repeatable fluid output using a minimum number of components and can be constructed entirely from plastic components (excepting the SMA wire) at a low cost. Furthermore, embodiments of the invention require very little power to operate (operating from battery power for portability) and are suitable for long term pump applications.

FIG. 1A is a longitudinal cross-section of an exemplary embodiment of the compact micropump showing the internal components. As illustrated herein, micropump embodiments of the present invention include specific components with unique structural properties (e.g. SMA wire) that are organized into specific configurations (e.g. SMA that is double back to enhance the work stroke). This design then allow for a compact design which is significantly smaller than existing pump designs, and in this way, overcomes certain limitations associated with the existing pumps. Preferred embodiments of the invention are typically constructed in a cylindrical form of approximately 15–25 millimeters (and more preferably about 21 millimeters) in diameter by approximately 15–25 millimeters (and more preferably about 19 millimeters) long, preferably with fluid intake and output at opposite axial ends. This design and arrangement of elements that allows the generation of extremely compact pump embodiments that overcome a number of difficulties associated with larger pump designs known in the art, and, for example, enables a convenient and inconspicuous infusion device to be constructed and used.

In the embodiment depicted in FIG. 1A, the fluid pump 100A includes an intake tube 102 to accept a fluid. The received fluid is drawn through the intake tube 102 by a negative pressure produced by expansion of the pump chamber 104. The intake valve 106 is designed to admit fluid from the intake tube 102 and substantially prevent any reflux into the intake tube 102 from the chamber 104. In the embodiment depicted in FIG. 1A the intake valve 106 is shown as a spring-loaded ball poppet with intake seating interface 108. The integral spring 110 extends from a stem of the intake valve 106. Fluid is output from the chamber 104 through an output valve 112 to an output tube 114. The output valve 112 operates to only allow fluid to exit the chamber 104 through the output tube 114 under a positive pressure from the chamber 104. In the embodiment of FIG. 1A, the output valve 112 is a spring loaded ball poppet using a compression spring 116 to hold the valve 112 closed along the output seat interface 118. Although the intake and output valves 106, 112 are shown as ball poppet valves, many other suitable valves can be used as will be described hereafter.

The chamber 104 is designed to expand and contract in volume as a piston 120 moves relative to the cylinder wall 122. A stop 124 limits travel of the piston 120 to control the maximum chamber volume. In this embodiment, the output valve 112 is housed within the piston 120 and moves with it. Fluid flows through the output valve 112 to the output tube 114, also coupled to the piston 120. In comparison, the intake valve 106 is coupled to the housing 134 and remains stationary while the pump 100A operates. A cylinder wall seal 126 prevents fluid from leaking out of the chamber 104 as the pump 100 operates.

Actuation of the pump 100 is provided by an SMA wire 128 and return bias spring 130 placed in opposition. The SMA wire 128 is threaded through the piston 120 and guided over guides 136A, 136B at one end to separate two separate anchors 132A, 132B at the distal end of the pump 100. The SMA wire 128 is guided to take large radius turns (relative to the wire diameter) to minimize binding of the SMA wire 128 as it contracts and expands.

As is known in the art, the allowable stroke for shape memory alloys is typically limited to a low percentage of the element length (e.g. less than 10%). Consequently, preferred embodiments of the invention disclosed herein address this property by employing a design that extends the effective length of the SMA wire 128, thereby increasing the work stroke generated the pump. Such embodiments of the invention can extend the total effective length of the SMA wire 128 by using a "doubled back" configuration. For example, the SMA wire 128 is doubled back from the piston 120 over the guides 136 at one end of the pump 100 to the anchors 132 at the other. In this way a greater operating stroke is achieved while still maintaining a very compact pump form.

Electrical connection is typically made to the SMA wire 128 at the ends, either integral to the anchors 103 or to free ends of the SMA wire 128 extending beyond the anchors 132. As the SMA wire 128 also functions as its own thermoelectric heater, the wire is typically electrically isolated so it does not short.

Figure 1B:
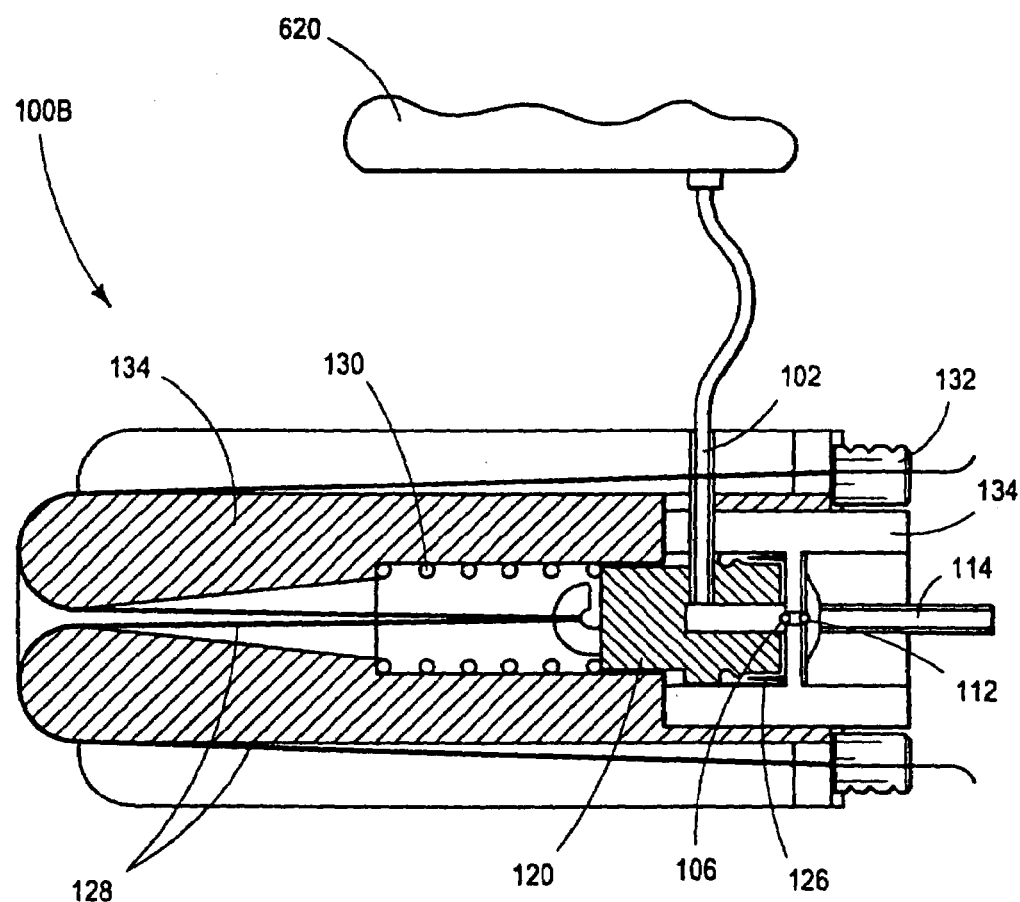
FIG. 1B is a longitudinal cross-section of another exemplary embodiment of the invention showing the internal components.

FIG. 1B is a longitudinal cross-section of another exemplary embodiment of the invention showing the internal components. Components of the pump 100B are referenced identically as those of pump 100A. Both pumps 100 operate in a similar manner, however, in pump 100B the output valve 112 and output tube 114 are disposed in the housing 134, while the intake tube 102 and intake valve 106 are disposed in the piston 120. In addition, in this pump 100B the intake tube 102 is positioned radial to the cylindrical housing 134. Either embodiment of the pump (FIG. 1A or FIG. 1B) undergoes a three-phase cycle including an "at rest", "intake stroke" and "injection stroke" phase.

It should also be understood that while the two exemplary pumps 100 illustrate typical designs. Other configurations are possible. For example, the intake and output valves 106, 112 can both be positioned in either the piston 120 or housing 134. If the intake and output valves 106, 112 are placed in the housing 134, there is no need for a flexible interface in the fluid conduit to accommodate the piston movement. In addition, the intake and output tubes 102, 114 can also be disposed in any direction from the pump housing, axial, radial or in between to facilitate fluid flow from a reservoir to a user.

Figure 2A:
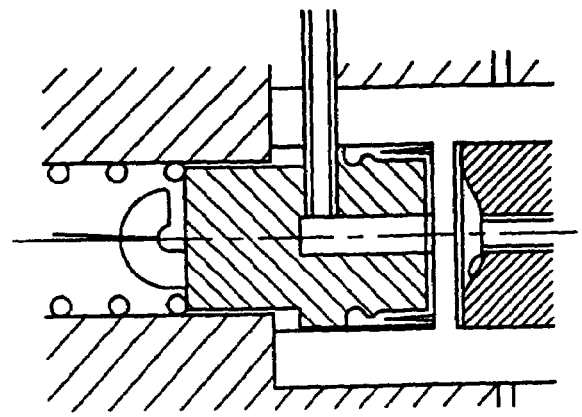
FIGS. 2A–2C illustrate the "at rest", "intake stroke" and "injection stroke" phases of the pumping cycle.
Figure 2B:
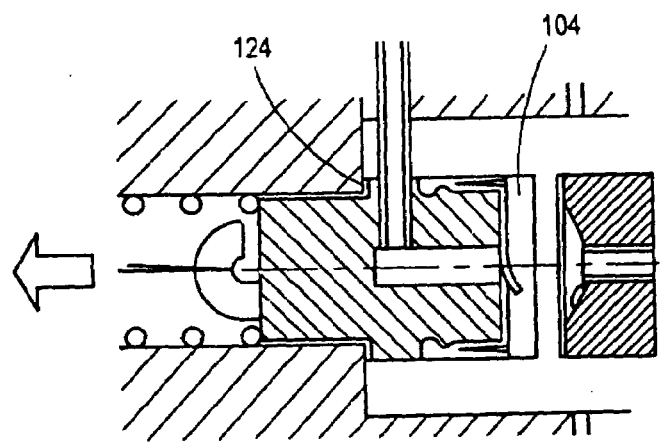
Figure 2C:
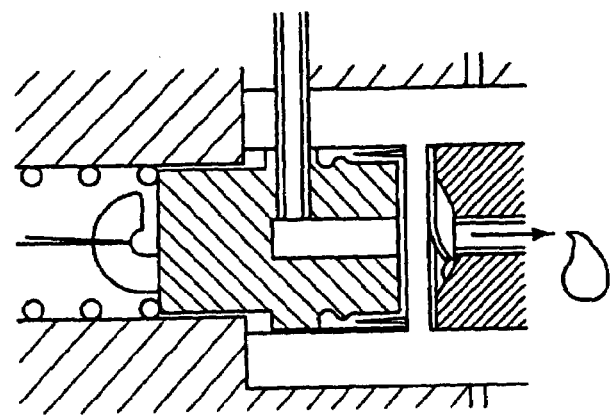

FIGS. 2A–2C illustrate the "at rest", "intake stroke" and "injection stroke" phases of the pumping cycle. FIG. 2A illustrates the "at rest" phase of the pumping cycle with the pump 100 in the home position. In this phase, both the intake and output valves 106, 112 are in the closed position. The SMA wire 128 is not energized and therefore in an easily deformable condition. Thus, it can be stretched to a length greater than the preset "memorized" shape.

FIG. 2B illustrates the "intake stroke" phase of the pumping cycle. Here, the SMA wire 128 is energized to a temperature at or above the transformation temperature. As a result, the SMA wire 128 contract to recover the "memorized" shape (i.e. a shorter length) and in doing so overcomes the bias spring 130 force and draws the piston 120 back to expand the pumping chamber 104 volume. In one embodiment, the chamber 104 volume changes from zero to approximately 1 ml. As the chamber 104 volume increases, negative pressure occurs in the chamber causing the intake valve 106 (e.g., a flap valve) to open as fluid is drawn in from the reservoir. When the chamber 104 volume reaches 1 ml, the piston hits the limit stop 124 and the chamber 104 is full. Power to the SMA wire 128 can now be eliminated. As the fluid pressure reaches equilibrium, the intake valve 106 closes.

FIG. 2C illustrates the "injection stroke" phase of the pumping cycle. After power to the SMA wire 128 is eliminated, the wire 128 begins to quickly cool. Upon reaching a temperature below the transformation temperature, the SMA wire 128 returns to a plastic condition. At this point the bias spring 130 force begins to deform the wire, stretching it, and drive out the fluid accumulated in the chamber 104 through the output valve 112. At this point, the pump is returned to the home position (as depicted in FIG. 2A) and the cycle may repeat to produce a pulsatile fluid flow output.

Figure 3A:
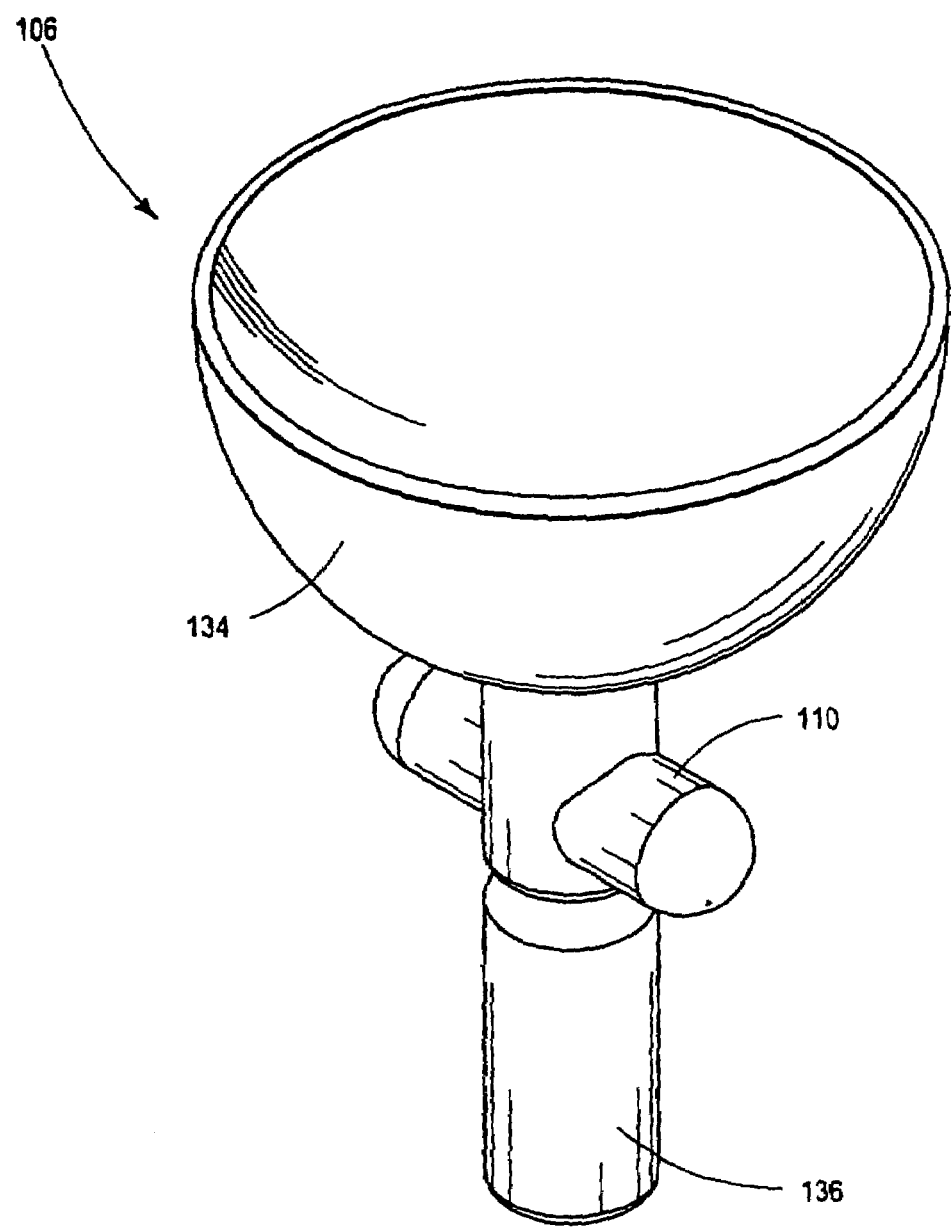
FIGS. 3A and 3B illustrate details of the intake and output valve components of one embodiment of the invention.
Figure 3B:
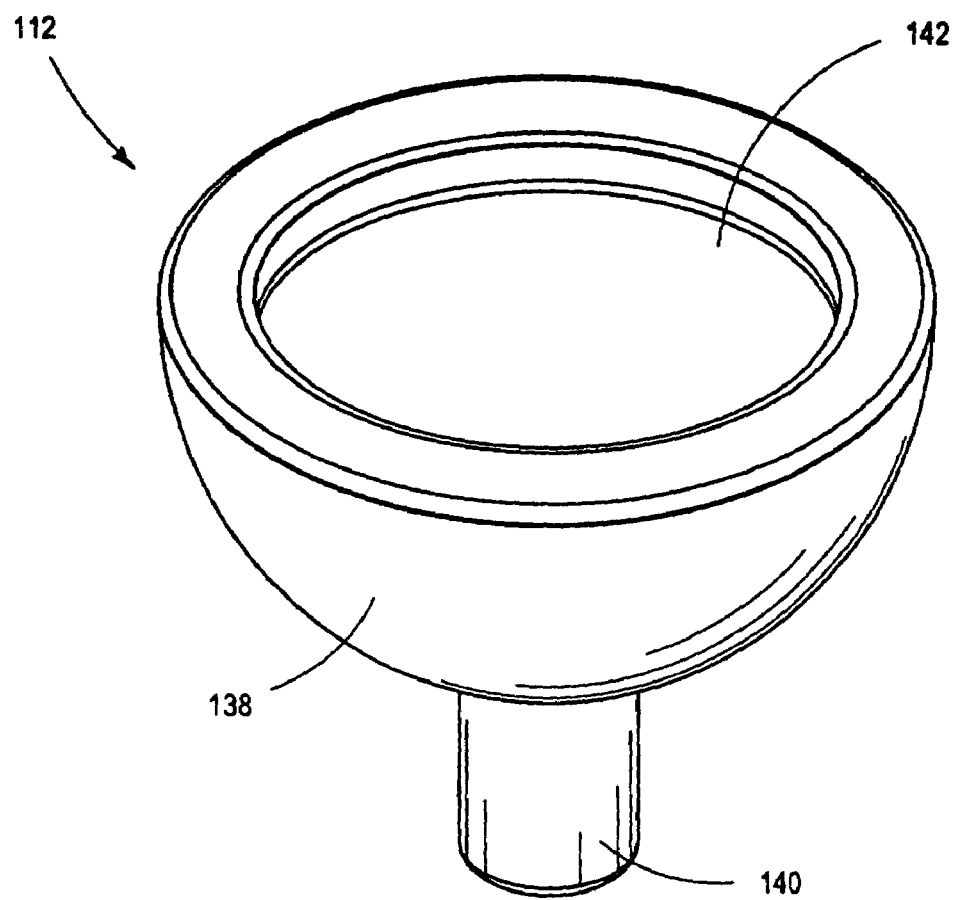

FIGS. 3A and 3B illustrate details of the intake and output valve components of the first exemplary embodiment of the invention. FIG. 3A illustrates the intake valve 106 of the pump 100A in its manufactured form. The intake valve 106 is constructed to include an integral spring 110, in the form of cantilevered arms, extending from a stem of the intake valve 106. In this embodiment, the valve 106 includes a spherical seating surface 134 which seals against the intake seating interface 108 in the pump 100A. A handling tail 136 can also be incorporated in the valve 106 to facilitate easy manipulation during assembly of the pump 100A. The tail 136 is then trimmed after assembly. In one embodiment, the valve 106 can be formed from silicon rubber to provide good sealing characteristics.

FIG. 3B illustrates the output valve 112 of the pump 100A. In this embodiment, the output valve 112 is also formed with a spherical seating surface 138 which seals against the output seating interface 118 in the pump 100A. The output valve 112 also includes a pilot stem 140 to position the valve 112 during assembly and operation of the pump 100A. In this valve embodiment, a counter bore 142 is provided to seat the compression spring 116 which holds the valve 112 closed. The output valve 112 can also be formed from silicon rubber to provide good sealing characteristics.

FIG. 3C illustrates details of the SMA wire 128 connection to the piston 120 for one embodiment of the invention. A coupler 144 is provided that attaches to the rear portion of the piston 120. The coupler 144 is cylindrical and includes a special curved cut, shaped to admit the SMA wire 128 from a radial surface of the coupler 144. When the SMA wire 128 is seated in the coupler 144, the wire 128 rides over a smooth large radius guide to facilitate unrestricted expansion and contraction of the SMA wire 128. An axial fluid path is also provided through the coupler which is not intersected by the cut so no leakage results. The coupler 144 can also include an external thread to interface with an internal thread on the piston 120. In addition, the coupler 144 can include a counter bore seat in bottom axial surface as best seen in cross section of FIG. 1A.

Figure 4A:
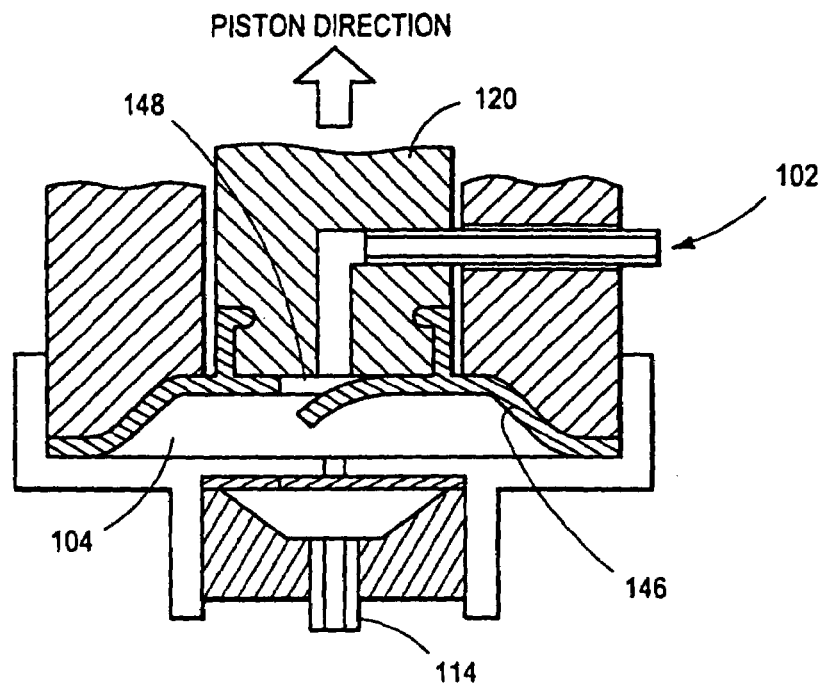
FIGS. 4A and 4B illustrate a further embodiment of the invention utilizing a diaphragm in place of the piston seal.
Figure 4B:
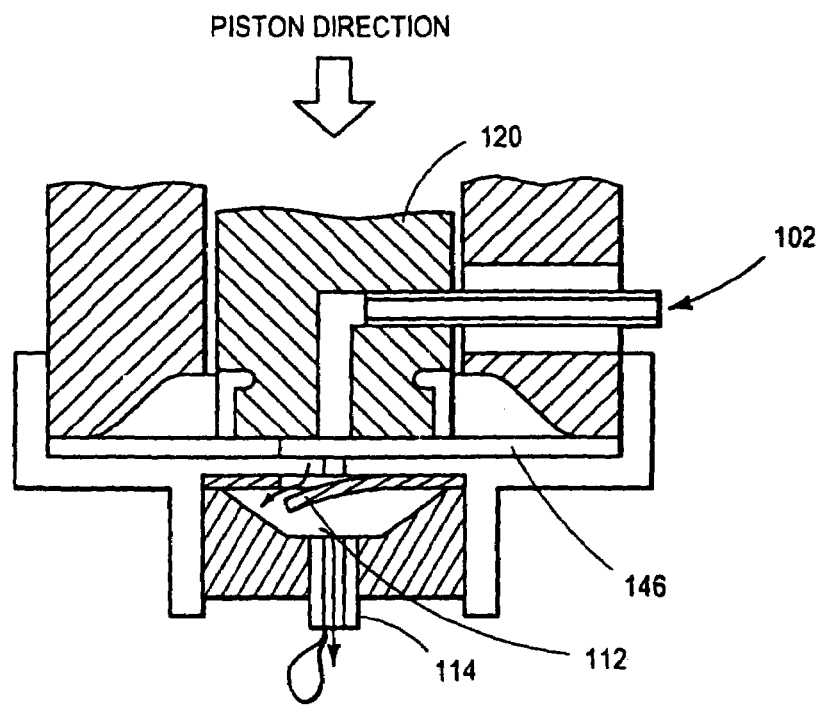

FIGS. 4A and 4B illustrate a further embodiment of the invention utilizing a diaphragm 146 to form the fluid chamber 104. FIG. 4A depicts a diaphragm chamber 104 fully expanded. FIG. 4B depicts the diaphragm chamber 104 collapsed. The diaphragm 146 eliminates the need for the separate piston seal 126. The diaphragm chamber 104 effectively creates a static (rather than dynamic) seal against fluid leakage. In either case, it is important that fluid does not leak from the chamber as the pump operates. As seen in FIG. 4A, the diaphragm 146 includes a piston attachment feature 148 which holds a center portion of the diaphragm 146 to the moving piston 120. Another portion of the diaphragm 146 is then fixed to the housing 134. As with previous embodiments, movement of the piston 120 expands and contracts the chamber 104. In the embodiment shown, the periphery of the diaphragm 146 is held trapped between the main housing structure and a separate housing component containing the output valve 112. The diaphragm 146 can also include an integral intake valve 106, such as a flap valve. In further embodiments, the diaphragm can be implemented as a closed bladder including both the intake and output valves 106, 112.

FIGS. 5A–5F illustrate some alternate embodiments of suitable intake and output valves. Each of the valves permit fluid flow under pressure in the direction indicated but close to block a reverse fluid flow under reverse pressure. FIG. 5A illustrates a rubber flap valve formed from a rubber sheet covering an orifice. FIG. 5B illustrates a free ball valve (i.e. not spring loaded). FIG. 5C illustrates a metal reed valve. FIG. 5D illustrates a spring-loaded ball valve using a compression spring. FIG. 5E illustrates a ball valve using a diaphragm to capture the ball. FIG. 5F illustrates a spring-loaded ball poppet valve with the spring integral to the poppet stem. The ball of the ball valve embodiments, can be formed from rubber or any other suitable material. The valves each vary in their performance characteristics. For example, the free ball valve will require more reverse pressure to close, but less forward pressure to permit fluid flow than the spring-loaded valves. Spring-loaded valves are normally closed and require a degree of forward pressure to open and permit flow.

Figure 9A:
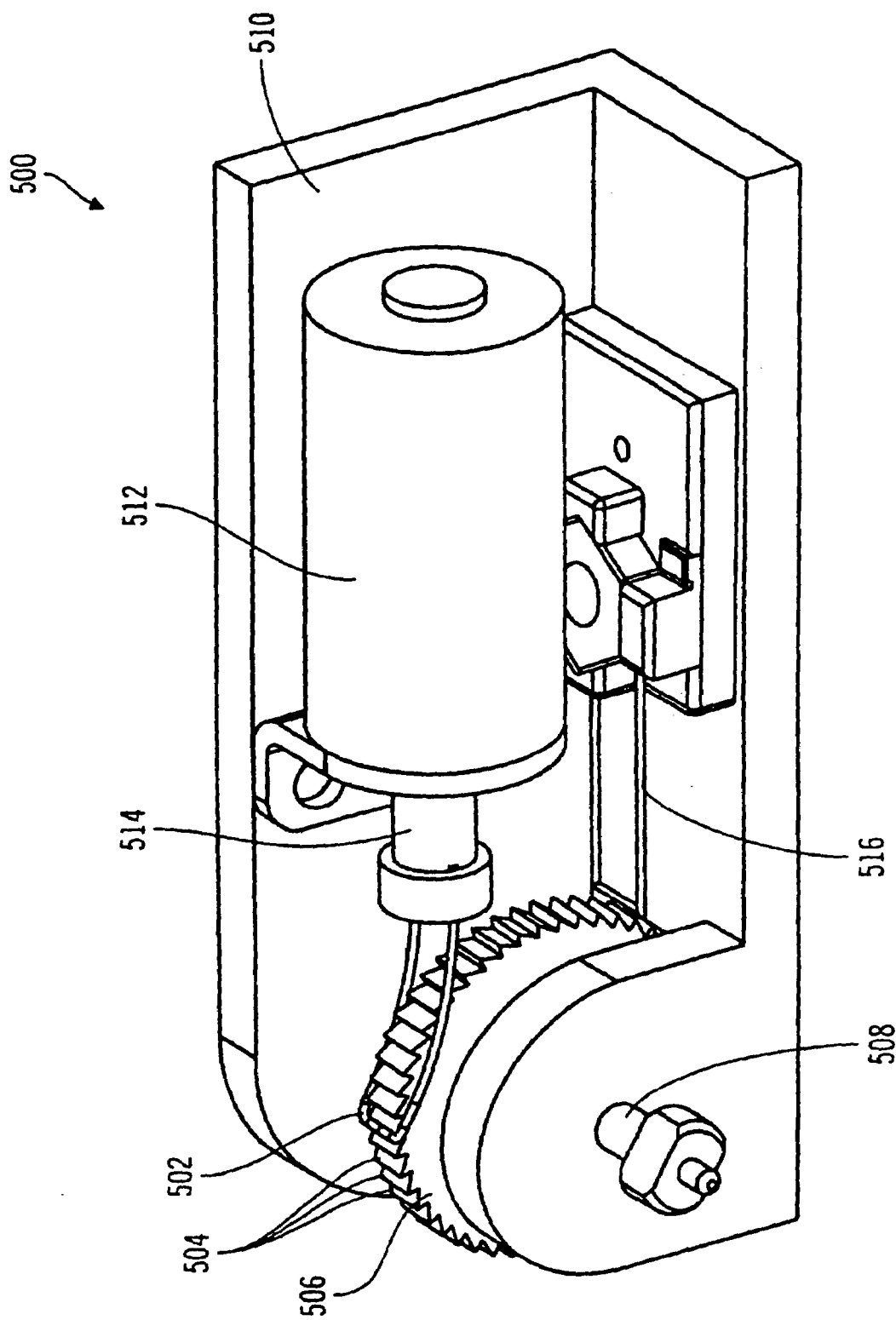
FIGS. 9A and 9B are perspective views of a drive mechanism in accordance with embodiments of the present invention.
Figure 9B:
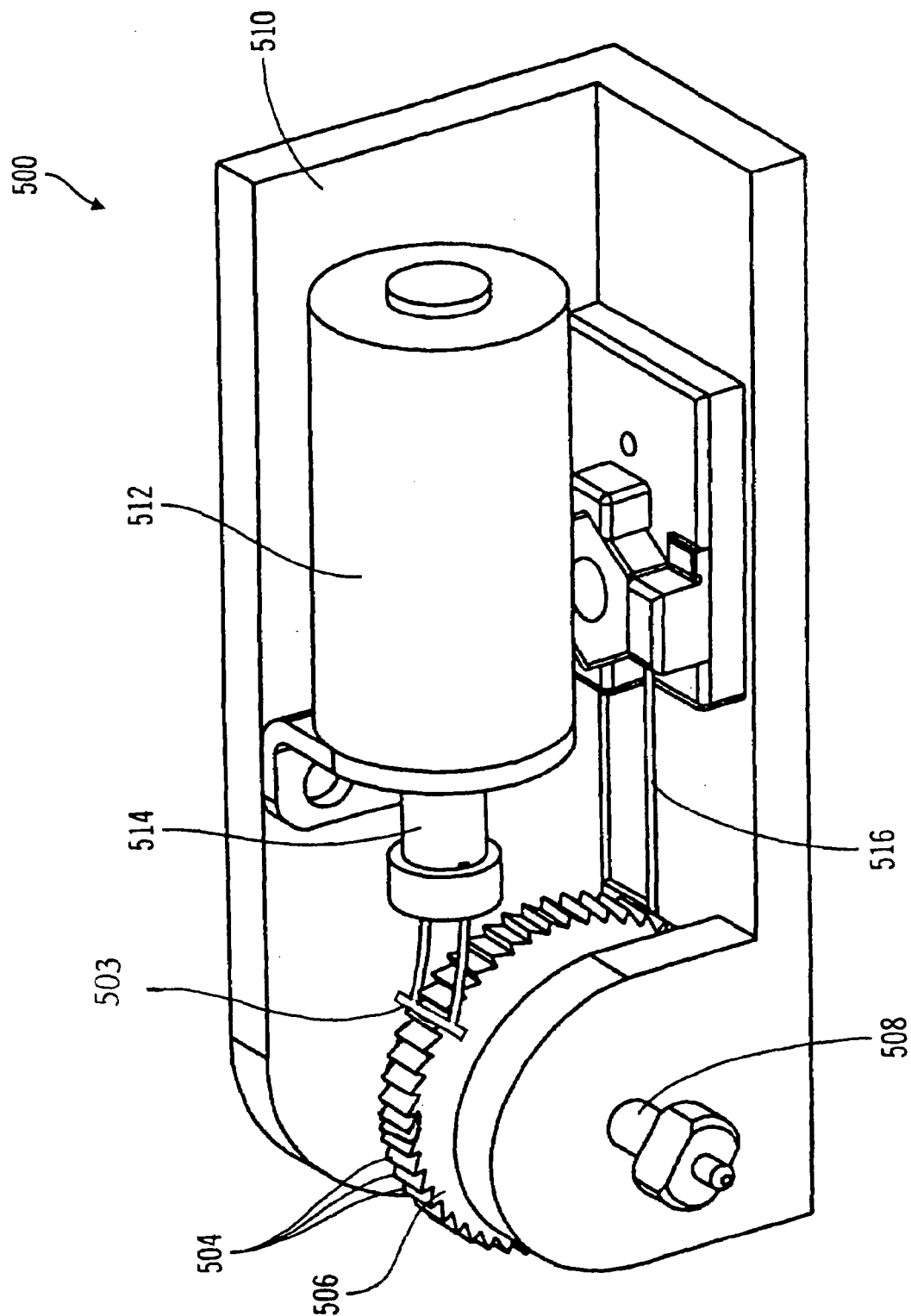

As discussed herein, embodiments of the present invention use shape memory materials as the actuator for the drive mechanism. However, the above-noted embodiments are not the only way to use shape memory materials for actuation of a drive mechanism. For example, FIG. 9A illustrates a drive mechanism 500 in accordance with one embodiment of the present invention. The drive mechanism 500 includes a shape memory material pull 502 that is actuated to contract and pull on teeth 504 of a gear 506, which in turn rotates and/or ratchets the gear 506 to drive the medication infusion pump mechanism. After the gear 506 is rotated, the shape memory material 502 is allowed to expand and slide over the next tooth 504 on the gear 506. Preferably, the gear 506 is rotatably mounted to a pin 508 that is secured to a support housing 510. The shape memory material is activated by a power supply 512 that is connected to control electronics 514 to adjust the shape of the shape memory material 502. To keep the gear from rotating backwards, a backstop pawl 516 engages with the teeth 504 of the gear 506 in a ratchet manner. FIG. 9B illustrates an alternative embodiment, where the shape memory material is a bar structure 503 or the like, that pushes on the teeth 504 of the gear, as opposed to pulling, to rotate the gear 506 and actuate the drive mechanism 500.

3. Miniature Self-Contained Drug Infusion Pump

Pump embodiments of the invention previously described can be further incorporated into infusion device systems. For example, further embodiments of the invention include a miniature, self-contained drug infusion pump for direct subcutaneous delivery of insulin for the treatment of Type II diabetes. Embodiments of the invention can be conveniently attached by adhesive directly to the skin of the user at the infusion site. FIGS. 6A–6D illustrate the system and operation of such a MINIPATCH pump.

Figure 6A:
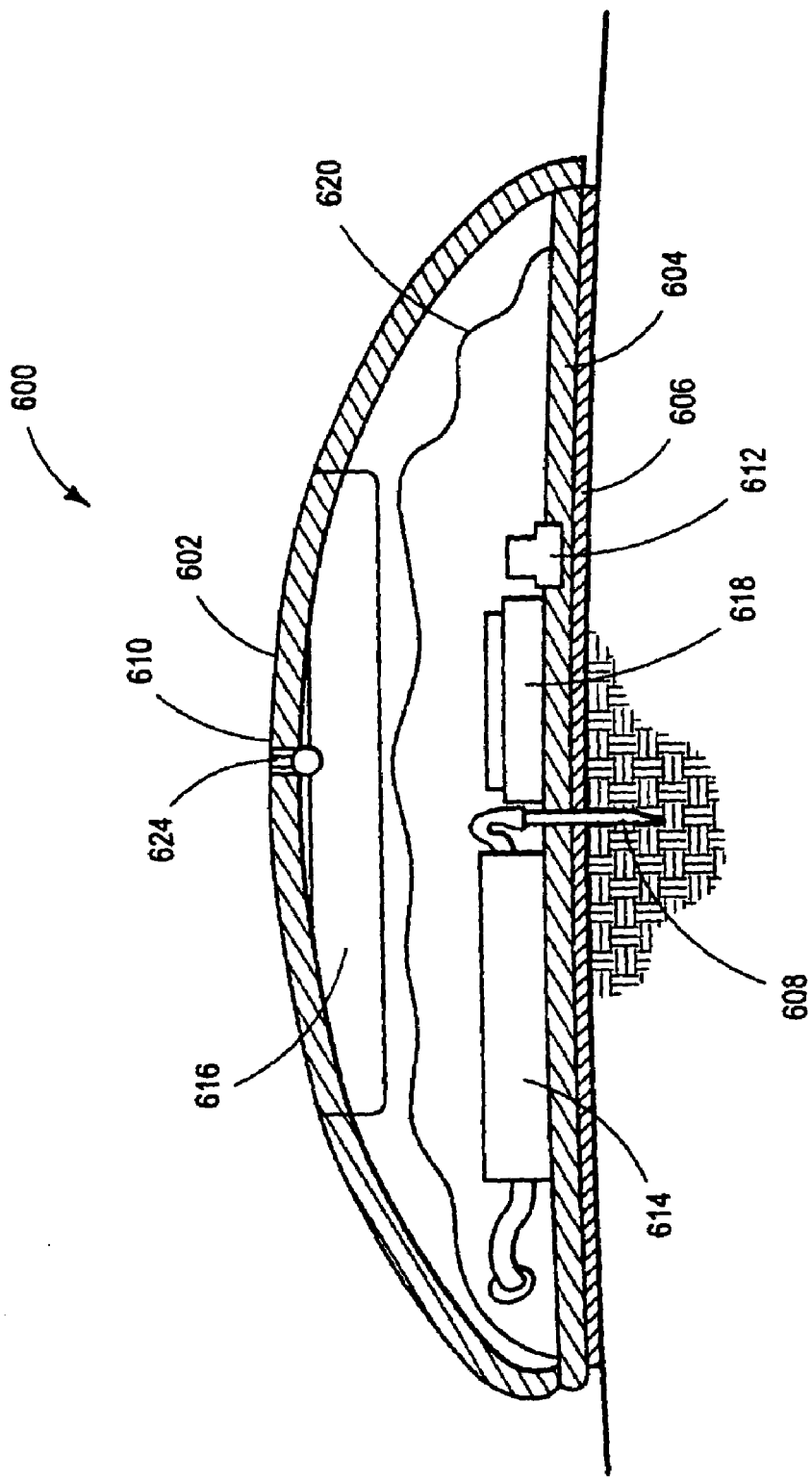
FIG. 6A illustrates a cross section view of a further embodiment of the invention employing the pump in a compact infusion device.

FIG. 6A illustrates a cross section view of a further embodiment of the invention employing the pump in an ultra-compact infusion device 600. The infusion device 600 enclosure is formed from a "turtle shell" cover 602 attached to the perimeter of a base plate 604. In operation, the infusion device 600 is placed directly on the skin, held by a pressure sensitive adhesive material 606 on the back of the base plate 604, at the infusion site of the user. An integral infusion set, including a piercing member 608 such as a needle, penetrates the skin for subcutaneous medication delivery.

Other related art infusion devices separate the infusion set from the infusion pump so that fluid is conveyed from the pump to a remote infusion site through a long conduit. This is done to facilitate control or programming by the user. In addition, these pumps (even relatively compact models) are still too heavy and bulky to be held directly at the infusion site. Embodiments of the invention, however, utilize an integral infusion set that is directly connected to the pump (i.e., not remote from the pump). Further, embodiments of the present invention also employ preprogrammed prescription electronics modules to minimize (or eliminate) the need for user interaction while the device is in use.

The enclosure also includes a vent 610 to accommodate environmental pressure changes and allow internal and external air pressure to equalize as fluid is driven out of the device 600. A fill port 612, such as a self-sealing rubber septum, is also provided in the enclosure so that the user can fill the device with medication prior to use.

Figure 6B:
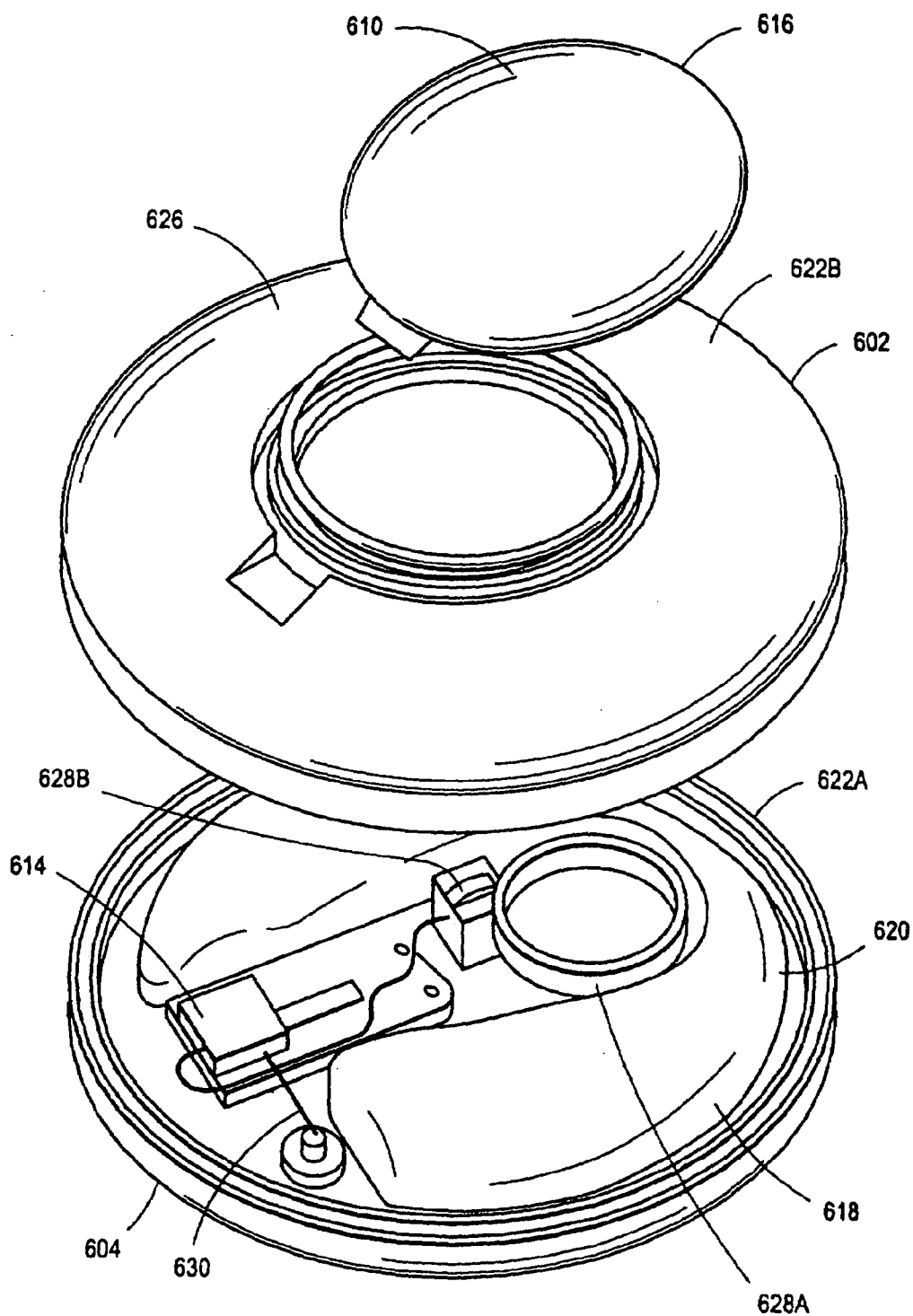
FIG. 6B illustrates an exploded view the compact infusion device.

FIG. 6B is a partially exploded view of the device 600 showing further detail of the internal components and the separate reusable electronics module 616. As the device 600 is specifically designed to be water resistant (such that a user may wear it while showering), seals 620 are used to prevent liquids from entering the device 600. The case and the removable electronics module are therefore fitted with rubber o-ring seals 622.

The enclosure houses a pump 614 (such as the SMA driven pump embodiments previously described), an electronics module 616 to control the pump 614, a battery 618 to power the pump 614 and a fluid reservoir 620. The fluid reservoir 620 can be constructed as a collapsible bag, formed to occupy the free space surrounding the pump 614 and battery 618 and capable of holding approximately 3.2 ml of fluid. The reservoir 620 can be sealed to the base plate 604 along a seam around its perimeter. The septum fill port 612 mounted in the base plate 604 directly accesses the reservoir 620. An input tube 630 provides a fluid path from the reservoir 620 to the pump 614.

In one embodiment of the device 600, the electronics module 616 is separable from the infusion device 600. The electronics module 616, programmed per an appropriate prescription for the user based upon individual insulin needs, can be supplied to different patients for use with the infusion device 600. Thus, the electronics module 616 can be distributed as a separate item.

In order for the medication fluid reservoir 620 to react to ambient atmospheric pressure and still maintain water resistance of the device, a breathable GORTEX vent membrane 624 or suitable alternative material can be employed over the vent 610. The infusion device 600 can be distributed as an unfilled, "dry" disposable unit without the electronics module 616. The programmed reusable electronics module 616 can be distributed as a separate item.

The reusable electronics module 616 can be further separable from the cover 602 to facilitate simple exchangeability of components. Electrical contacts 628 connect to the electronics module 616 to the pump 614 and/or battery 618 when it is installed into cover 602 of the device 600. The electronics module 616 can be attached to the cover 602 with snap fit latch 626. The latch can also function as a locating tab so that the electronics module 616 is properly oriented to engage the electrical contacts 628. The o-ring seal 622B keeps the interface watertight. A similar feature is used to keep the cover 602 oriented and sealed to the base plate 604.

The functional elements of the infusion device 600 can also be alternately divided between the cover 602 and base plate 604 halves as well. For example, in one embodiment, the vent 610 can be placed on a disposable portion of the device 600, such as the cover 602 or base plate 604. This arrangement allows the user to regularly replace the vent membrane 624 material, which may become dirty or clogged over a long period. In addition, the battery 618 can be housed with the removable electronics module 616. In this case, the battery 618 is either separately replaceable or rechargeable.

Figure 6C:
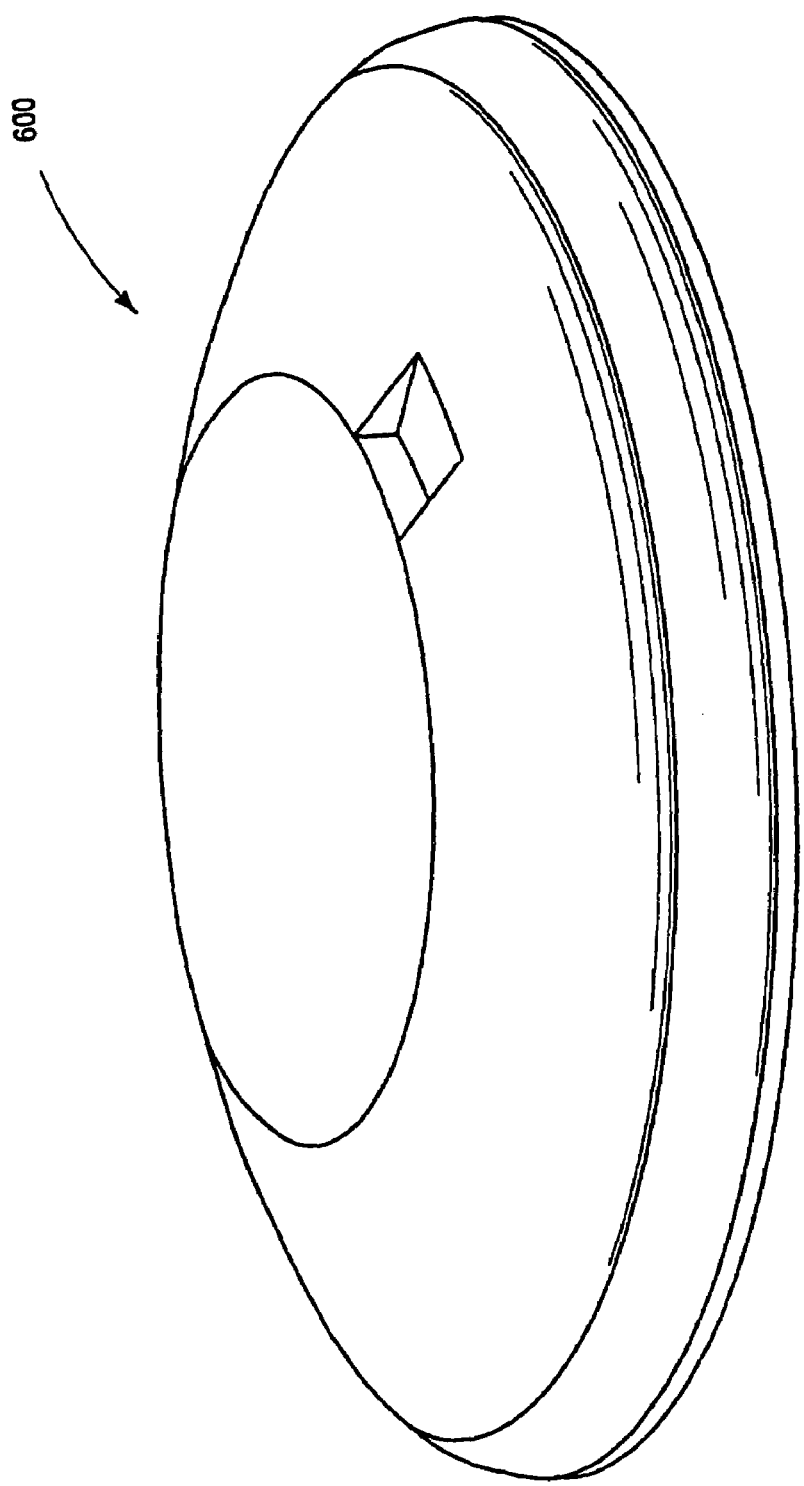
FIG. 6C illustrates a exterior view of the compact infusion device.
Figure 7B:
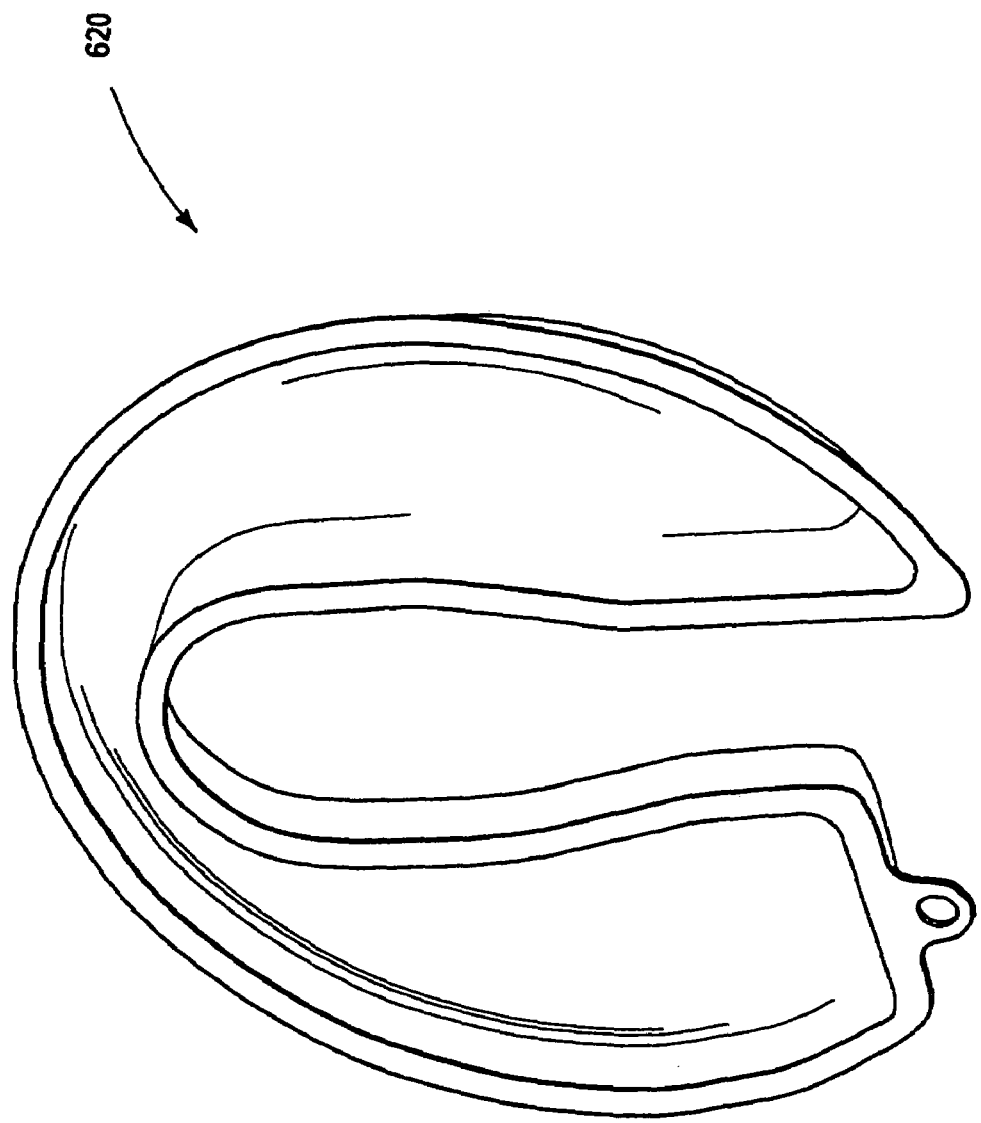
FIG. 7B illustrates a view of the fluid reservoir of the compact infusion device.

FIG. 6C illustrates an exterior view of the compact infusion device and FIG. 6D illustrates an exterior side view of the compact infusion device. In one embodiment, the ultra compact device 600 is approximately two inches in diameter and 0.425 inches thick, with a fluid capacity of approximately 3.2 ml. FIG. 7A illustrates a view of the electronics module 616 of the compact infusion device 600. FIG. 7B illustrates an interior view of the fluid reservoir 620 of the compact infusion device 600.

4. Exemplary Methods for Pumping Fluid

Figure 8A:
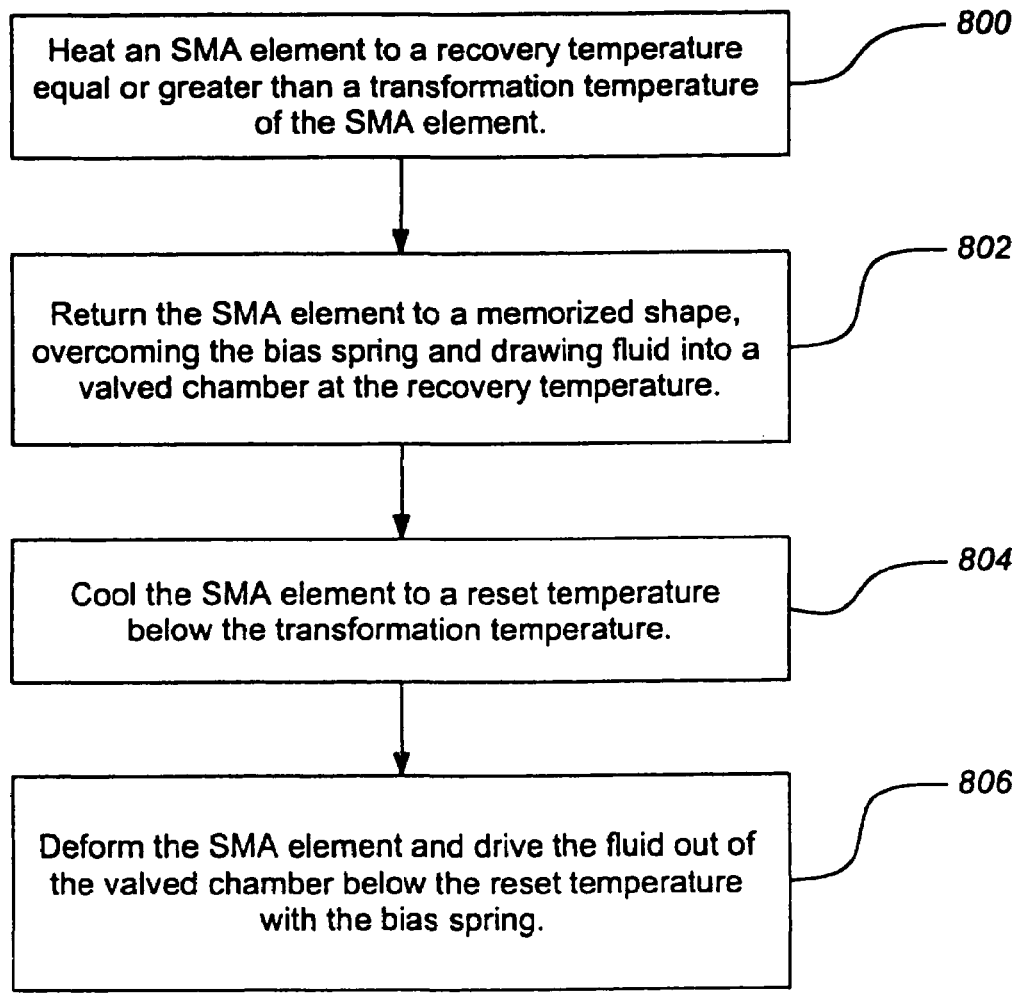
FIG. 8A illustrates a method where the injection stroke is actuated by the bias spring.
Figure 8B:
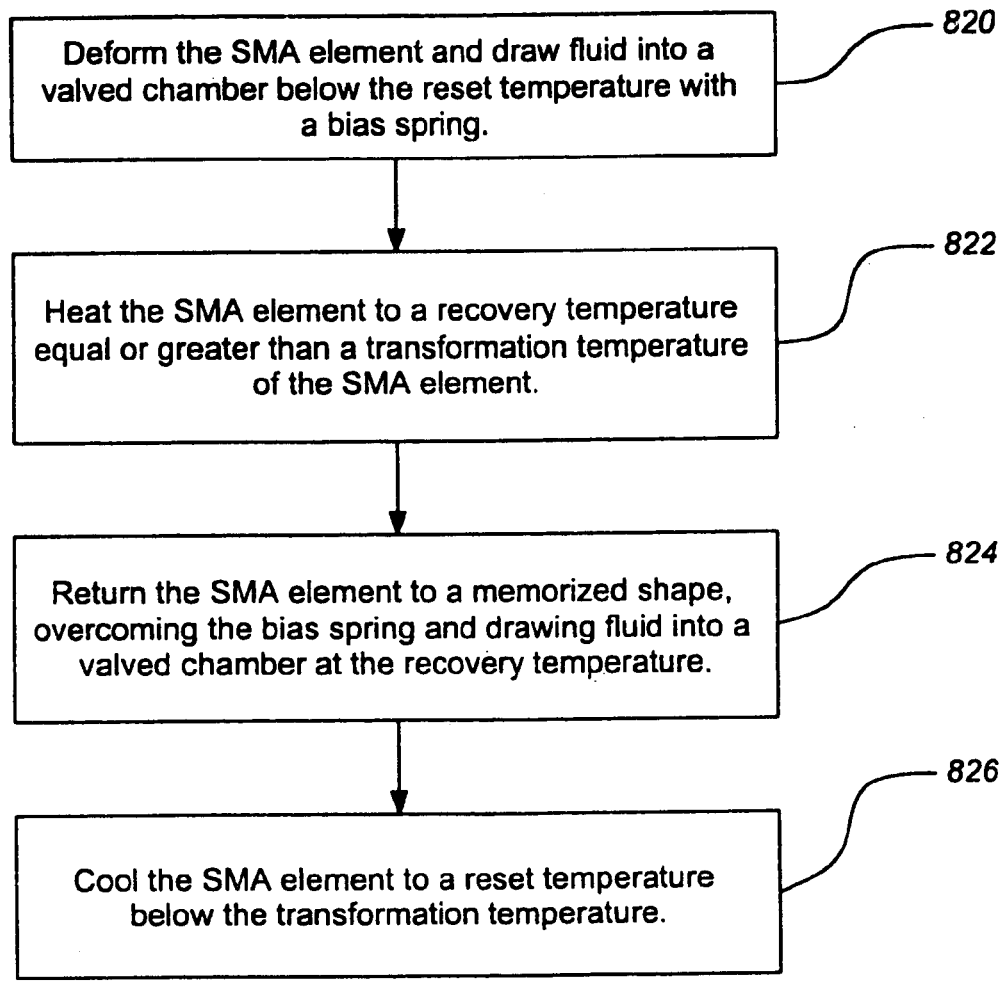
FIG. 8B illustrates a method where the injection stroke is actuated by the recovery of the SMA element at or above the transformation temperature.

FIGS. 8A and 8B are flowcharts of some exemplary methods for pumping fluid. FIG. 8A illustrates a method where the injection stroke (i.e., fluid driven out of the chamber) is actuated by the bias spring. FIG. 8B illustrates a method where the injection stroke is actuated by the recovery of the SMA element at or above the transformation temperature.

FIG. 8A is a flowchart of an exemplary method for pumping a fluid where the injection stroke is driven by the bias spring. The method begins at block 800 where an SMA element is heated to a recovery temperature equal or greater than a transformation temperature of the SMA element. At block 802, the SMA element overcomes the bias spring to return to a memorized shape and draw fluid into a valved chamber at the recovery temperature. At block 804, the SMA element is cooled to a reset temperature below the transformation temperature. At block 806, the bias spring deforms the SMA element and drives fluid out of the valved chamber below the reset temperature. The method is then repeated to produce a pulsatile fluid flow.

Alternately, FIG. 8B is a flowchart of an exemplary method for pumping a fluid where the injection stroke is driven by SMA element. The method begins at block 820 where a bias spring deforms the SMA element and draws fluid into a valved chamber at a reset temperature below the transformation temperature of the SMA element. At block 822, an SMA element is heated to a recovery temperature equal or greater than the transformation temperature. At block 824, the SMA element overcomes the bias spring to return to a memorized shape and drive fluid out of the valved chamber at the recovery temperature. At block 826, the SMA element is then cooled to the reset temperature. The method is then repeated to produce a pulsatile fluid flow.

The previously detailed embodiments of the invention operate according to the method of FIG. 8A, however, an alternate arrangement of components will allow the injection stroke to be driven by the SMA element. For example, by disposing the valved chamber on the opposite side of the SMA wire and biased spring, an apparatus functioning according to the method of FIG. 8B is obtained.

CONCLUSION

This concludes the description including the preferred embodiments of the present invention. The foregoing description including the preferred embodiment of the invention has been presented for the purposes of illustration and description. It is not intended to be exhaustive or to limit the invention to the precise form disclosed. Many equivalent modifications and variations are possible in light of the above teaching.

It is intended that the scope of the invention be limited not by this detailed description, but rather by the claims appended hereto. The above specification, examples and information provide a description of the manufacture and use of the apparatus and method of the invention. Since many embodiments of the invention can be made without departing from the scope of the invention, the invention resides in the claims hereinafter appended.

What is claimed is:

1. An apparatus, comprising:
   a gear engagement member comprising a shape memory wire, the wire capable attaining at least two different material conditions, a first material condition below a transformation temperature and a second material condition above a transformation temperature, wherein the wire attains a memorized configuration such that the wire can produce a work stroke as a consequence of a transition between the first and second material conditions;
   a gear adapted to engage the gear engagement member, wherein the gear engagement member is in direct contact with teeth on the gear;
   a fluid pump coupled to the gear such that when the gear is engaged with the gear engagement member and actuated, the fluid pump generates a fluid flow from the work stroke produced by the wire; and
   a fluid conduit adapted to couple the fluid pump to a fluid medication reservoir.

2. The apparatus of claim 1, wherein the gear engagement member comprises a pull that rotates the gear to generate fluid flow.

3. An apparatus comprising:
   a gear engagement member comprising a shape memory wire, the wire capable attaining at least two different material conditions, a first material condition below a transformation temperature and a second material condition above a transformation temperature, wherein the wire attains a memorized configuration such that the wire can produce a work stroke as a consequence of a transition between the first and second material conditions;
   a gear adapted to engage the gear engagement member;
   a fluid pump coupled to the gear such that when the gear is engaged with the gear engagement member and actuated, the fluid pump generates a fluid flow from the work stroke produced by the wire; and
   a fluid conduit adapted to couple the fluid pump to a fluid medication reservoir, wherein the gear engagement member comprises a pull that rotates the gear to generate fluid flow, and wherein the pull contacts and pulls on teeth on the gear to rotate the gear.

4. The apparatus of claim 3, wherein after the gear is rotated, the pull expands and slides over a tooth on the gear.

5. The apparatus of claim 1, further comprising a backstop pawl adapted to engage with teeth on the gear so that the gear rotates in a single direction.

6. The apparatus of claim 1, wherein the fluid pump delivers fluid medication from a fluid medication reservoir to a user.

7. The apparatus of claim 1, further comprising a power supply coupled to the shape memory wire to thermoelectrically induce at least the transformation temperature in the wire.

8. The apparatus of claim 1, wherein the gear is rotatably mounted to a pin that is secured to a housing.

9. A fluid delivery system, comprising
a reservoir;
a fluid pump for receiving a fluid from the reservoir and driving the fluid out a conduit;
an electronic circuit for controlling delivery of the fluid with the pump;
a gear engagement member comprising a shape memory wire, the wire capable attaining at least two different material conditions, a first material condition below a transformation temperature and a second material condition above a transformation temperature, wherein the wire and attains a memorized configuration such chat the wire can produce a work stroke as a consequence of a transition between the first and second material conditions;
a gear adapted to engage the gear engagement member, wherein the gear engagement member is in direct contact with teeth on the gear and the fluid pump is coupled to the gear such that when the gear is engaged with the gear engagement member and actuated, the fluid pump generates a fluid flow from the work stoke produced by the wire;
an enclosure housing the reservoir, gear, gear engagement member, pump and electronic circuit; and
an infusion set directly coupled to the conduit.

10. The fluid delivery system of claim 9, wherein the gear engagement member comprises a pull that engages and rotates the gear to generate fluid flow.

11. A fluid delivery system, comprising
a reservoir;
a fluid pump for receiving a fluid from the reservoir and driving the fluid out a conduit;
an electronic circuit for controlling delivery of the fluid with the pump;
a gear engagement member comprising a shape memory wire, the wire capable attaining at least two different material conditions, a first material condition below a transformation temperature and a second material condition above a transformation temperature, wherein the wire and attains a memorized configuration such that the wire can produce a work stroke as a consequence of a transition between the first and second material conditions;
a gear adapted to engage the gear engagement member, wherein the fluid pump is coupled to the gear such that when the gear is engaged with the gear engagement member and actuated, the fluid pump generates a fluid flow from the work stroke produced by the wire;
an enclosure housing the reservoir, gear, gear engagement member, pump and electronic circuit; and
an infusion set directly coupled to the conduit,
wherein the gear engagement member comprises a pull that engages and rotates the gear to generate fluid flow, and wherein the pull contacts and pulls on teeth on the gear to rotate the gear.

12. The fluid delivery system of claim 11, wherein after the gear is rotated, the pull expands and slides over a tooth on the gear.

13. The fluid delivery system of claim 9, further comprising a backstop pawl adapted to engage with teeth on the gear so that the gear rotates in a single direction.

14. The fluid delivery system of claim 9, wherein the pump delivers fluid medication from a reservoir to a user.

15. The fluid delivery system of claim 9, further comprising a power supply coupled to the wire to thermoelectrically induce at least the transformation temperature in the wire.

16. A method of pumping fluid, comprising the steps of:
subjecting a shape memory wire to a first material condition, wherein the wire comprises a gear engagement member and is capable attaining at least two different material conditions, a first material condition below a transformation temperature and a second material condition above a transformation temperature, and wherein the wire and attains a memorized configuration such that the wire can produce a work stroke as a consequence of a transition between the first and second material conditions; and
subjecting the wire to a second material condition,
wherein a gear is coupled to a fluid pump and the gear engagement member is in direct contact with teeth on the gear such that when the gear is engaged with the gear engagement member and actuated, the fluid pump generates a fluid flow from the work stroke produced by the wire as a consequence of a transition between the first and second material conditions.

17. The method of claim 16, wherein the gear engagement member comprises a pull that engages and rotates the gear to generate fluid flow.

18. A method of pumping fluid, comprising the steps of:
subjecting a shape memory wire to a first material condition, wherein the wire comprises a gear engagement member and is capable attaining at least two different material conditions, a first material condition below a transformation temperature and a second material condition above a transformation temperature, and wherein the wire and attains a memorized configuration such that the wire can produce a work stroke as a consequence of a transition between the first and second material conditions; and
subjecting the wire to a second material condition,
wherein a gear is coupled to a fluid pump such that when the gear is engaged with the gear engagement member and actuated, the fluid pump generates a fluid flow from the work stroke produced by the wire as a consequence of a transition between the first and second material condition,
wherein the gear engagement member comprises a pull that engages and rotates the gear to generate fluid flow, and wherein the pull contacts and pulls on teeth on the gear to rotate the gear.

19. The method of claim 16, wherein after the gear is rotated, the pull expands and slides over a tooth on the gear.

20. The method of claim 16, wherein the fluid comprises a medication.

21. The method of claim 16, wherein the fluid is pumped from a medication reservoir to a user.

22. The method of claim 16, wherein subjecting the wire to a material condition comprises heating or cooling the wire.

23. The method of claim 22, wherein the subjecting the wire to a material condition comprises heating end is performed using a power supply coupled to the wire.

24. The method of claim 22, wherein subjecting the wire to a material condition comprises providing a pulsing current to the wire to incrementally heat and cool the wire.

* * * * *